(12) United States Patent
Hofius et al.

(10) Patent No.: US 10,543,339 B2
(45) Date of Patent: Jan. 28, 2020

(54) CATHETER DECOUPLING DEVICE

(71) Applicants: SRI INTERNATIONAL, Menlo Park, CA (US); Chunyuan Qiu, Menlo Park, CA (US)

(72) Inventors: Jonathan Hofius, Menlo Park, CA (US); Chunyuan Qiu, Menlo Park, CA (US); Manish Kothari, Menlo Park, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 0 days.

(21) Appl. No.: 15/683,291

(22) Filed: Aug. 22, 2017

(65) Prior Publication Data

US 2017/0368308 A1    Dec. 28, 2017

Related U.S. Application Data

(63) Continuation of application No. PCT/US2016/019954, filed on Feb. 26, 2016.

(60) Provisional application No. 62/121,279, filed on Feb. 26, 2015.

(51) Int. Cl.
*A61M 25/00* (2006.01)
*A61M 5/168* (2006.01)
*A61M 39/10* (2006.01)
*A61M 39/20* (2006.01)

(52) U.S. Cl.
CPC .... *A61M 25/0097* (2013.01); *A61M 5/16813* (2013.01); *A61M 39/1011* (2013.01); *A61M 39/20* (2013.01)

(58) Field of Classification Search
CPC ...... A61M 2025/0098; A61M 25/0097; A61M 39/10; A61M 39/1011; A61M 39/20; A61M 5/16813
See application file for complete search history.

(56) References Cited

U.S. PATENT DOCUMENTS

2009/0149814 A1   6/2009   Bailey et al.
2009/0163818 A1   6/2009   Zelenka et al.

*Primary Examiner* — Imani N Hayman
(74) *Attorney, Agent, or Firm* — Ballard Spahr LLP

(57) ABSTRACT

Devices, systems and methods are used to decouple proximal movement of a catheter supply lead or tubing from the tissue-embedded catheter. A catheter decoupling device comprises a catheter hub, sled and track, wherein the hub comprises a proximal end configured to receive a catheter fluid supply device, and a distal end configured to receive a catheter, the sled receives and retains the hub, the track receives and retains the hub; and, the hub has a limited range of back-and-forth motion relative to the track.

18 Claims, 8 Drawing Sheets

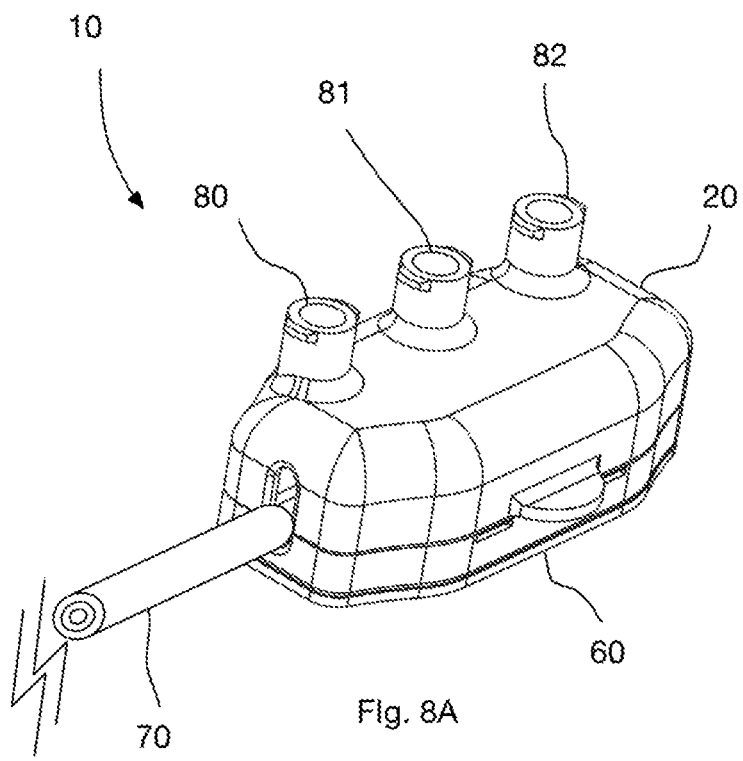
Fig. 8A
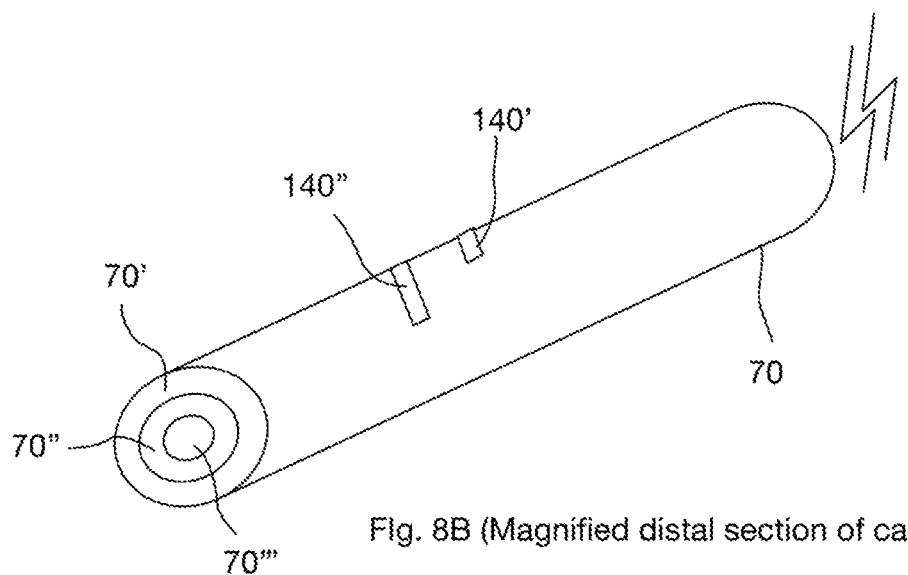
Fig. 8B (Magnified distal section of catheter 70)

CATHETER DECOUPLING DEVICE

This application is a continuation of PCT/US16/19954; filed Feb. 26, 2016, which claims priority to Ser. No. 62/121,279; filed Feb. 26, 2015.

This invention was made with government support under grant 1P50FD003782 awarded by the Department of Health and Human Services. The government has certain rights in this invention.

INTRODUCTION

In the practice of health care, there are numerous procedures where a catheter is placed within the body and is used as a conduit to either deliver therapeutic agents such as but not limited to drugs or to extract bodily fluids such as but not limited to blood. In some cases the catheter is used for both functions; to deliver agents and to extract fluids. In some of these procedures, it is necessary to ensure that the distal tip of the catheter remain stationary or relatively stationary at a particular location within the body. Such situations arise for example when a catheter is used to deliver anesthetic agents to a particular site within the body. In particular, in a continuous peripheral nerve block procedure, a catheter is inserted into the body for an extended period of time such as for 48 or 72 hours. A pump placed external to the body delivers anesthesia on a continuous basis to a site within the body. Typically, these types of procedures are used to provide relief from pain for example after a major orthopedic surgery. The distal end of the catheter is placed closed to a nerve that may be involved in transmitting the pain sensation. An anesthetic is delivered to the area close to the nerve, which if done appropriately, relieves the patient of the pain. In these situations, it is important to prevent the catheter from migrating away from the intended region. If migration occurs, the nerve block may become ineffective and the pain symptoms may return.

US2015/0306350 discloses an anchoring nerve block catheter having an anchoring mechanism at the distal end that prevents or minimizes the migration, including a skin attachment device to allow limited catheter motion and decouple the distal locking mechanism to minimize translation of motion from muscle or skin to the distal tip of the catheter; see, FIG. 2. However, another need arises when the proximal end of the catheter is considered. Conventionally the proximal end is coupled through a coupler to utility tubing that supplies the drug. Also conventionally, the proximal end of the catheter including the coupler is taped down or wrapped in a compression bandage so that it does not move relative to the skin. In this situation, the motion of both the distal end and the proximal end is restricted. If the patient ambulates or tries to ambulate, one or both end of the catheter may experience a stress as the actual length between the two ends may change due to ambulation but the length of the catheter does not change due to the anchoring mechanisms. This may lead to tissue tear and or migration of the distal end; in this case the block may become ineffective. On the proximal side, tissue bruising may occur which may lead to further complications.

We perceived desirability for a coupling mechanism on the proximal end of anchored nerve block catheter systems that allows for patient ambulation. Furthermore, we perceived the desirability for a coupling mechanism that allows patient ambulation in other situations as well, even when anchored catheters are not being utilized. For example, a patient with an IV inserted in a vein in a bend of the body such as in front of the elbow, may feel constricted in being able to move his or her arm. A coupling mechanism that allows for ambulation of the arm would allow the patient to feel less constricted.

SUMMARY OF THE INVENTION

The invention provides a decoupling system that allows a limited range of motion of the proximal end of the catheter. The decoupling system may be located between the proximal end of the catheter and the utility tubing and may be coupled or attached temporarily to the skin at the catheter exit site. This configuration allows a catheter with anchored at both ends to be utilized as the risk of stressing the anchor sites at either end is minimized or eliminated. This configuration also allows the length between the distal anchor site and the proximal anchor site to change allowing the patient to ambulate without risk of the catheter dislodging. The decoupling mechanism may also be able to absorb external forces and impacts, such as changing of the utility tubing or accidental pulling of the utility tubing. The decoupling mechanism may be designed to have varying amounts of motion. The range of distance that the decoupling mechanism allows may differ by application, location on body and purpose. The predetermined allowed range of motion in the decoupling motion may range from zero to the maximum anticipated distance needed for each particular application. For example, in femoral nerve blocks one can expect larger motion during hip flexion, so the range of motion that the decoupler needs to handle is larger than, for example, the range of motion you might expect to need to handle in an interscalene brachial plexus block. In most continuous peripheral nerve blocks, the distance that the proximal end of the catheter may be allowed to change between zero to five centimeters. In addition to being able to accommodate patient ambulation, the decoupling mechanism described below allows for different sized catheters. For example, in the embodiment with a sled that moves within a channel, one can adjust the channel length, for example, to create varying "size" decouplers for different medical applications.

The subject catheters include any elongate device that is introduced into a body cavity or tissue to deliver fluids, medications, electricity, sensors, or imaging technology. Examples include intravenous catheters, nerve block catheters, pacemaker leads, neurostimulation electrodes, Hickman catheters, NG tubes, catheters that reside in the spine such as for functional anesthetic discogram, peritoneal dialysis catheters, Foley catheters, any anchoring catheter, a variety of surgical drain catheters, and imaging scopes. The catheter can have a single lumen or multiple lumens that allow single or bidirectional movement of fluids, medications, electricity, etc.

The invention provides for minimizing or preventing the dislodgement or the migration of the an embedded catheter that may be caused due to motion of various entities such as but not limited to patient motion and supply tubing motion. In embodiments:

the catheter may have an anchor at its distal end;

the minimization or prevention may be achieved by a decoupling device that may generally consist of a mechanism that prevents or minimizes motion of the proximal end of the catheter. In an embodiment the mechanism comprises coupling the proximal end of a catheter to a movable platform which in turn may be coupled to tubing that can flex and/or stretch so that the motion of the entities may be taken up by the tubing rather than the proximal end of the catheter. Further, in addition to being able to move lengthwise, the movable platform may have the ability to move side to side or up and down to accommodate the various motions that the proximal end may encounter;

the decoupling device may or may not have a lid;

the decoupling device has a lid, the tubing may be coiled around a support column which may be rigid or rotating;

the decoupling device may have one or multiple input ports;

the decoupling device may have a mechanism to adjust for the various sizes of the catheter;

the decoupling device may be coupled to other components such as but not limited to in-line filters and sensors; and/or a sensor may monitor if the range of motion of the movable components of the decoupling device was exceeded, and if so a warning may be sent.

The invention provides a catheter decoupling device comprising a catheter hub, sled and track, wherein: the hub comprises a proximal end configured to receive a catheter fluid supply device, and a distal end configured to receive a catheter; the sled receives and retains the hub; the track receives and retains the hub; and the hub has a limited range of back-and-forth motion relative to the track.

In embodiments:

the hub further has a limited range of side-to-side and/or up-and-down motion relative to the track;

the limited range of motion is up to 50 mm;

the device further comprises a base, wherein the track is attached to, or is an integral part of the base;

the device further comprises a base and a lid, wherein the track is attached to, or is an integral part of the base, and the lid is configured to cover the hub, sled and track, wherein the lid may be hinged and/or press-lockable to the base;

the proximal end of the hub is configured to receive the catheter fluid supply device via a flexible or stretchable tubing connected to the hub via a connector (such as a luer connector) and connected to the catheter fluid supply device via an inlet port (such as in the lid), wherein the device may further comprise a bar around which the flexible or stretchable tubing is coiled; see, e.g. FIG. 5;

the device further comprises a tensioned or tensionable movable block configured to retain within the device catheters of varying sizes; see, e.g. FIG. 6; and/or the proximal end of the hub is configured to receive the catheter fluid supply device via a flexible or stretchable tubing connected to the hub via a connector and connected to the catheter fluid supply device via an inlet port, wherein the catheter fluid supply device is one of multiple (such as 2, 3, 4, 5 or 6) fluid supply devices, and the inlet port is one of multiple (such as 2, 3, 4, 5 or 6) inlet ports (see, e.g. FIG. 7), which may be connected to corresponding multiple lumens of the catheter, wherein each lumen terminates in a distinctly located exit port; see, e.g. FIGS. 8A, 8B; and/or wherein the catheter comprise at least inner and outer multimaterial sheaths, wherein the inner surface of the inner sheath comprises a lubricious material (e.g. PTFE), and/or wherein the inner sheath comprises an embedded coil (providing echogenicity, anti-kinking properties, rigidity, durability and/or strength).

The invention also provides method of using and making the subject decoupling devices, including, connecting the proximal end of the hub to the catheter fluid supply device and the distal end of the hub to the catheter, wherein the device decouples the catheter from movement, particularly on the proximal side of the device; and assembling and connecting the hub, sled and track to form the decoupling device.

The invention specifically provides all combinations of the recited embodiments, as if each had been laboriously individually set forth.

BRIEF DESCRIPTION OF THE DRAWINGS

FIG. 8A: Devise with multiple inlet ports connected to corresponding multiple lumens of the catheter; FIG. 8B: Lumens terminate in a distinctly located exit ports.

DETAILED DESCRIPTION OF PARTICULAR EMBODIMENTS AND EXAMPLES THEREOF

Figure 1:
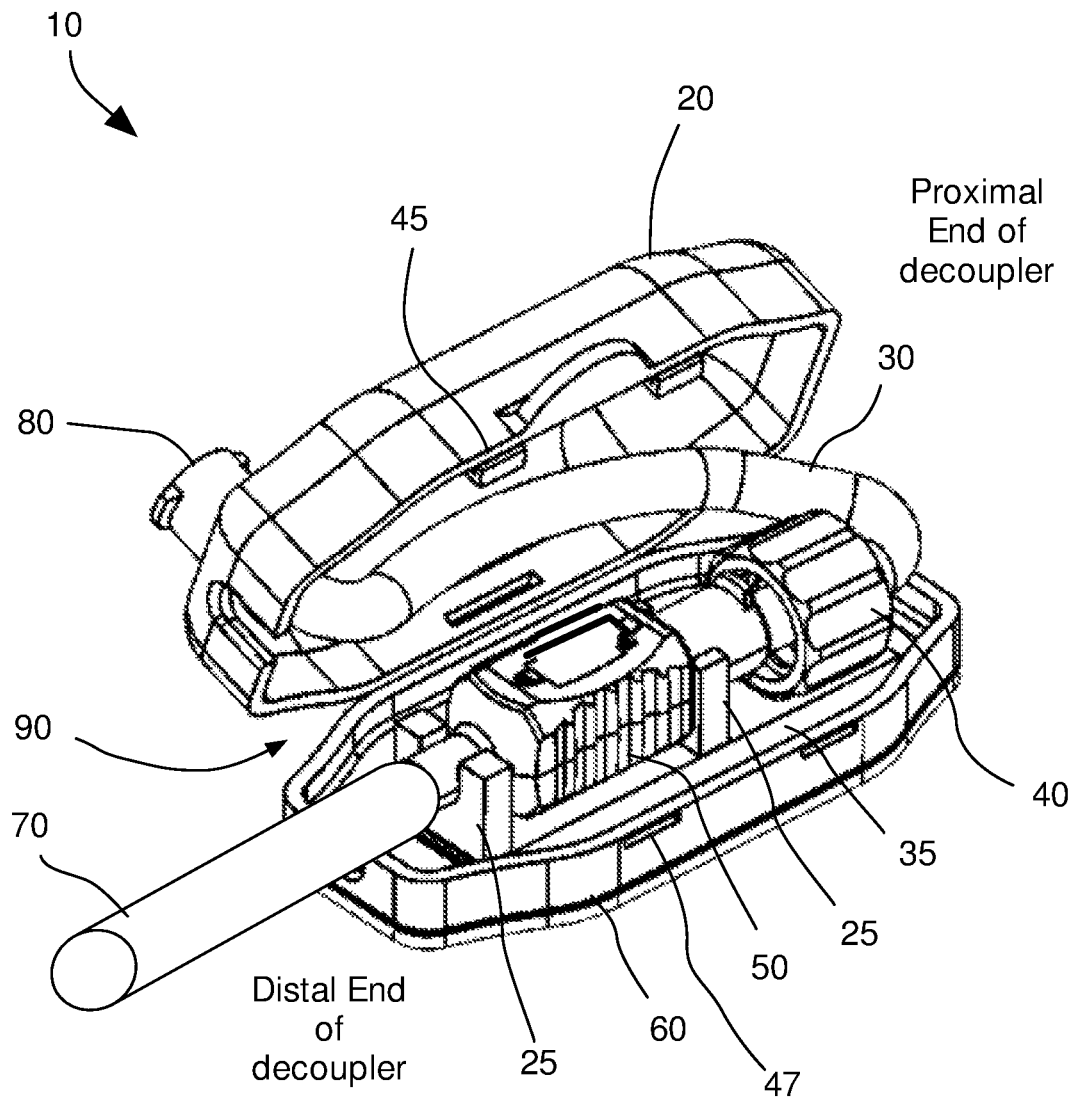
FIG. 1. One configuration of the decoupling device.

FIG. 1 illustrates one configuration of the decoupler, 10. This decoupler may be placed proximal to the exit location of an embedded catheter, between the catheter and the utlity tubing or other delivery devices. In this configuration, the catheter 70 may be coupled to a catheter hub 50. The catheter hub 50 may be placed within a sled 25; the distal and the proximal ends of the sled are visible in the figure and are both enumerated as 25. The sled may be positioned on a track 35 such that the sled may have some freedom of movement generally between the proximal end and the distal end of the decoupler. The track may be also so designed that some freedom of motion may be allowed side to side. In some versions, the tracks may be further designed to allow some up and down motion a well. As will be evident as more of the decoupler is described, this freedom of motion imparted to the sled is one component of the design of the decoupler that prevents, minimizes or eliminates motion of the catheter due to an external motion such as the motion of the patient or the motion of the supply devices.

Referring back to FIG. 1, the track 35 may be coupled to the base 60 of the decoupler using known methods such as but not limited to gluing or securing with screws. The track may also be an integral piece of the base. Since the track is coupled to the base, when assembled, the sled and the catheter hub are also coupled to the base through the track. More details will be provided with regards the base in later sections. Referring now to the proximal section of the catheter hub, it may be coupled to a flexible or stretchable tubing 30 (or flexible and stretchable) via a connector such as a luer connector 40. The flexible or stretchable (or both) tubing may then be routed to a lid 20 which may have an inlet port 80. The tubing may be coupled to the inlet port 80. Port 80 may be further coupled to supply devices such as but not limited to utility tubing or syringes. The lid 20 may be coupled to the base 60 by means of a hinge 90. A locking mechanism such as 45 and 47 may be provided such that the lid can be press locked onto the base. In a further design consideration, the base may be coupled to a double sided, biocompatible adhesive surface at its bottom surface; this allows the entire device 10 to be coupled to the skin of the patient, in proximity of the catheter entry site. Alternatively, the base need not have the adhesive surface; the entire device (except the inlet port 80) may be simply secured by biocompatible tape or dressing as is currently done to secure catheters or intravenous tubes or other similar devices.

In operation, when the lid is locked on to the base, the tubing 30 along with the sliding catheter hub prevents or eliminates motion of the catheter due to external motion. As an example, considering a case of a continuous nerve block catheter which is anchored at its distal end, if the patient flexes his or her limb, the proximal end of the catheter may experience motion. Assuming that this motion is towards the distal end, if the device 10 is coupled to the catheter, the catheter hub slides distally; the tubing 30 may allow this motion it may be designed to have sufficient slack for this motion to occur. Thus it can be seen how the device 10 decouples external motion and prevents the catheter from experiencing undue stress.

Figure 2:
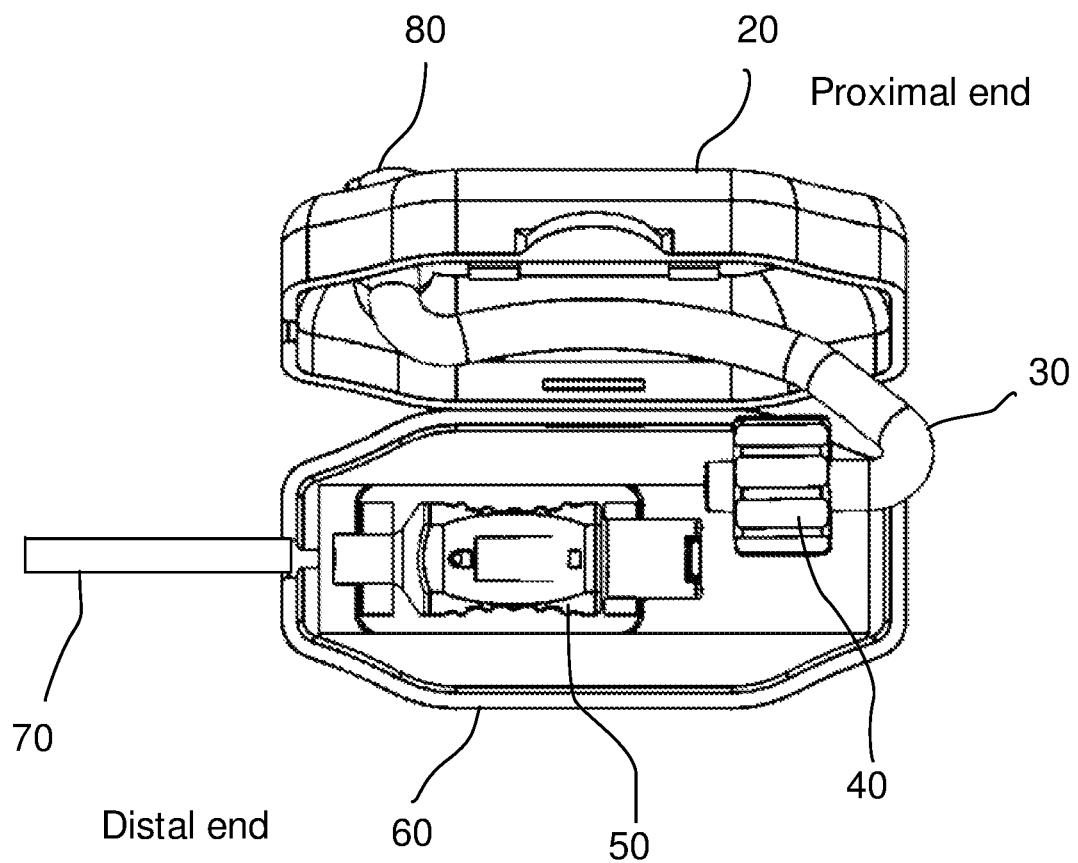
FIG. 2: Top view of the configuration a decoupling device.

FIG. 2 shows the top view of device 10. In this figure, the luer connector is shown disconnected from the catheter hub 50 for clarity. The configuration of the catheter hub and of the other components may be better appreciated in this figure.

Figure 3:
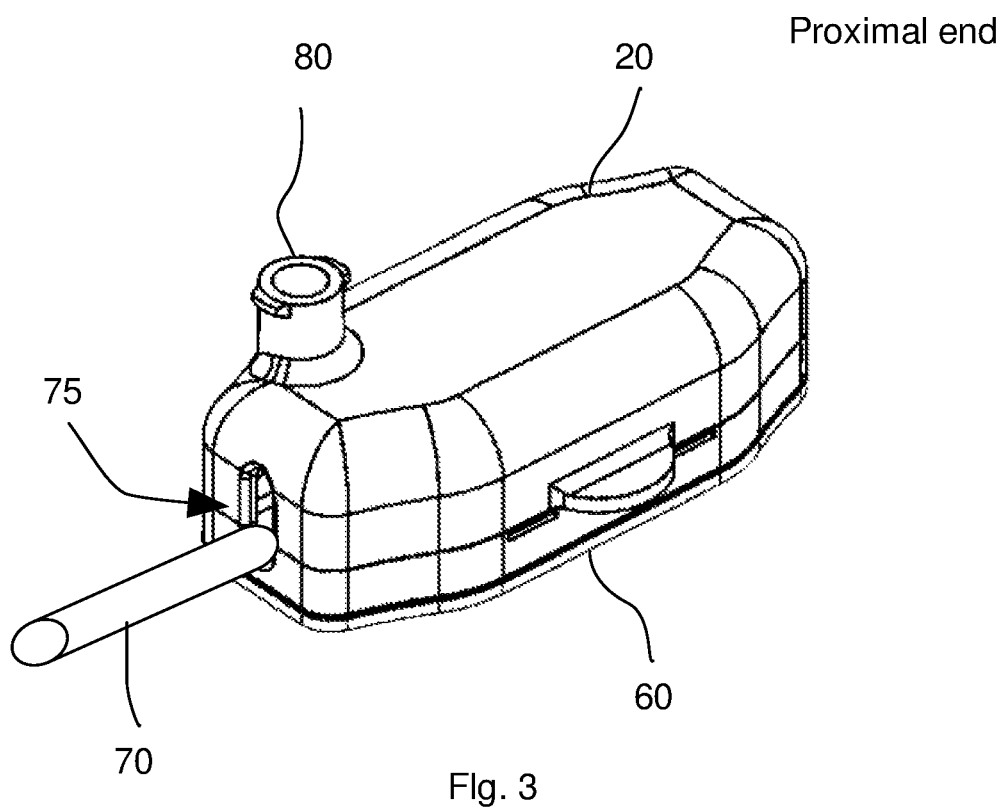
FIG. 3: Decoupling device wherein the lid is shut.

FIG. 3 illustrates the device when the lid 20 is closed. As specified above, the device 10 may be secured to the skin in various ways. If a dressing is used, to secure the device, the dressing may have a pre-cut hole to accommodate the inlet port 80. Alternatively, the dressing or other biocompatible tape may be applied to the entire surface except the inlet port. It is also to be noted that although the inlet port is located on top of the device, in alternate designs, the inlet port may be placed in other locations such as but not limited to the side of the device. This figure also clearly illustrates the exit hole for the catheter lumen 75. This exit hole may be designed in such a manner that it may accommodate catheters with various diameters from 0.25 F to 18 F. In addition to accommodating the various catheter sizes, the width of the exit hole may be made large enough to accommodate for motion of the catheter that may arise due to angulation during positioning. The exit hole may be as large as twice the size of the largest expected diameter of 18 F. Other sizes are not excluded.

Figure 4:
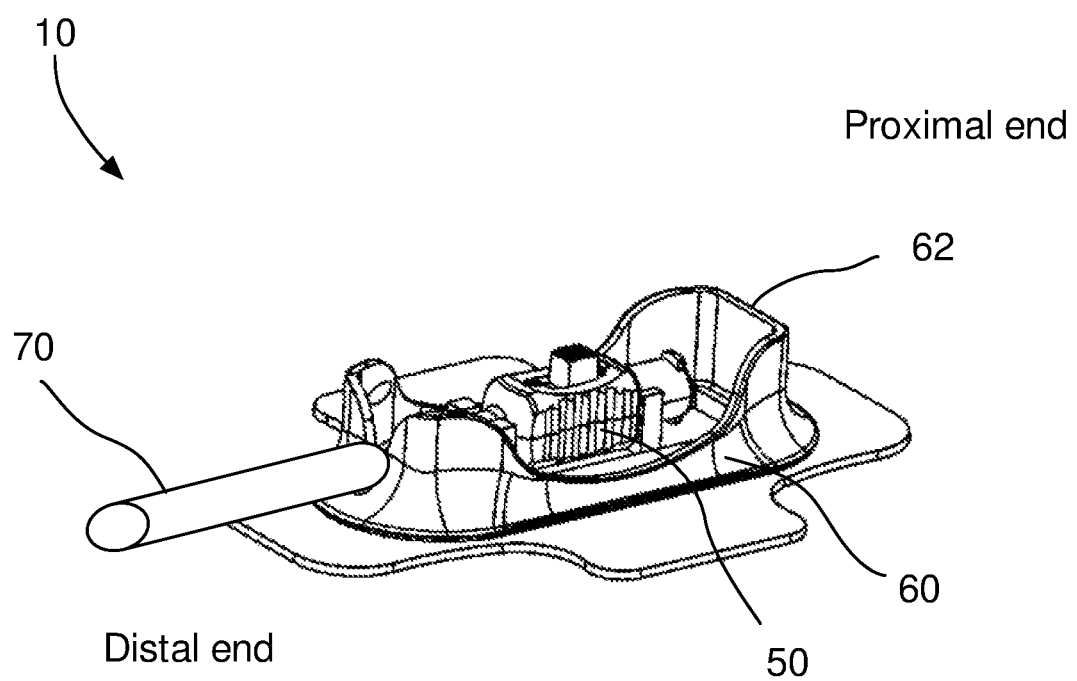
FIG. 4: Another configuration of the decoupling device.

Another configuration of the decoupling device is illustrated in FIG. 4. In this configuration the device 10 does not have a lid. Wall 62 of base 60 may be made tall so that the tubing 30 and the luer connector 40 may be located against the wall on the inside of the device. Since the configuration illustrated in FIG. 4 does not have the inlet port 80, the tubing to connect to the catheter hub may be the same as the supply tubing. Hence, the supply tubing may be coiled up and placed against wall 62. The top of this configuration may be covered by a biocompatible tape or dressing. Again, the side walls of the base may be designed to be tall enough that enough clearing is provided between the tape and the catheter hub such that the movement of the catheter hub is not restricted.

Figure 5:
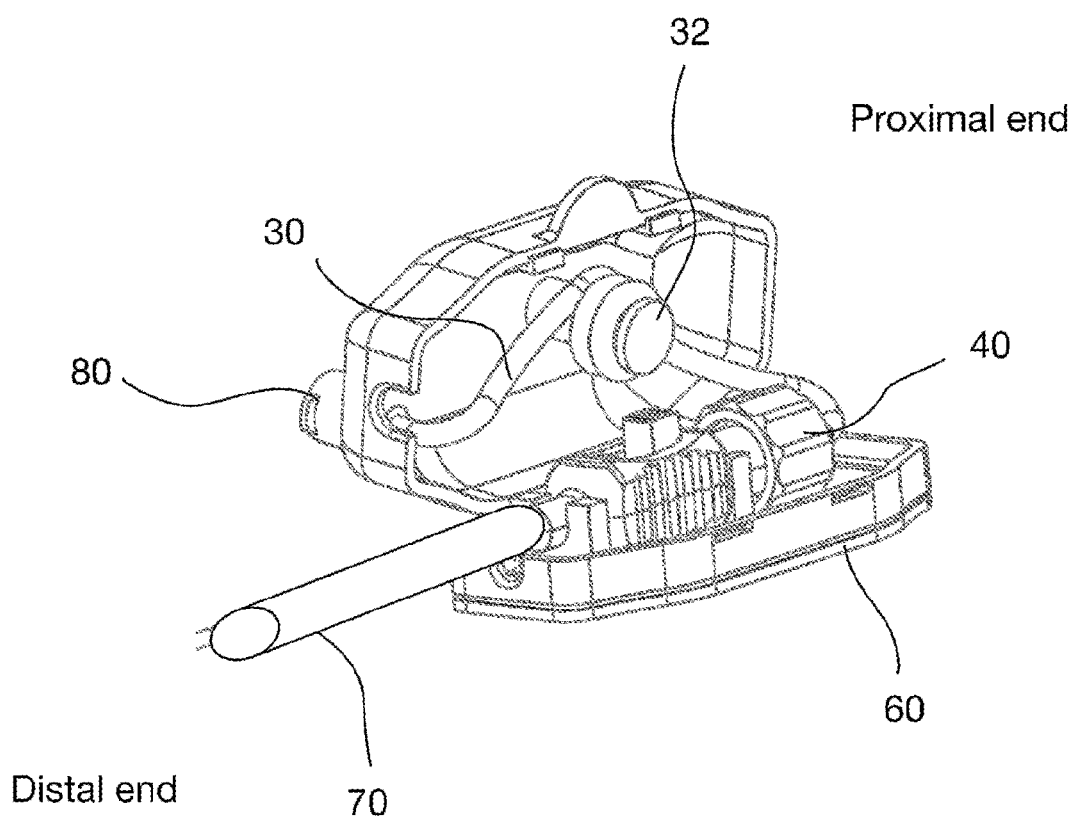
FIG. 5: Configuration of the decoupling device where a coiled method is used.

Yet another configuration is illustrated in FIG. 5. Here the flexible/stretchable tubing may be coiled around a cylindrical bar 32. The bar may be a static surface or it may be a freely rotating surface. This configuration may minimize or eliminate the bunching of the tubing 32 as movement is experienced by the catheter hub and the sled.

Figure 6:
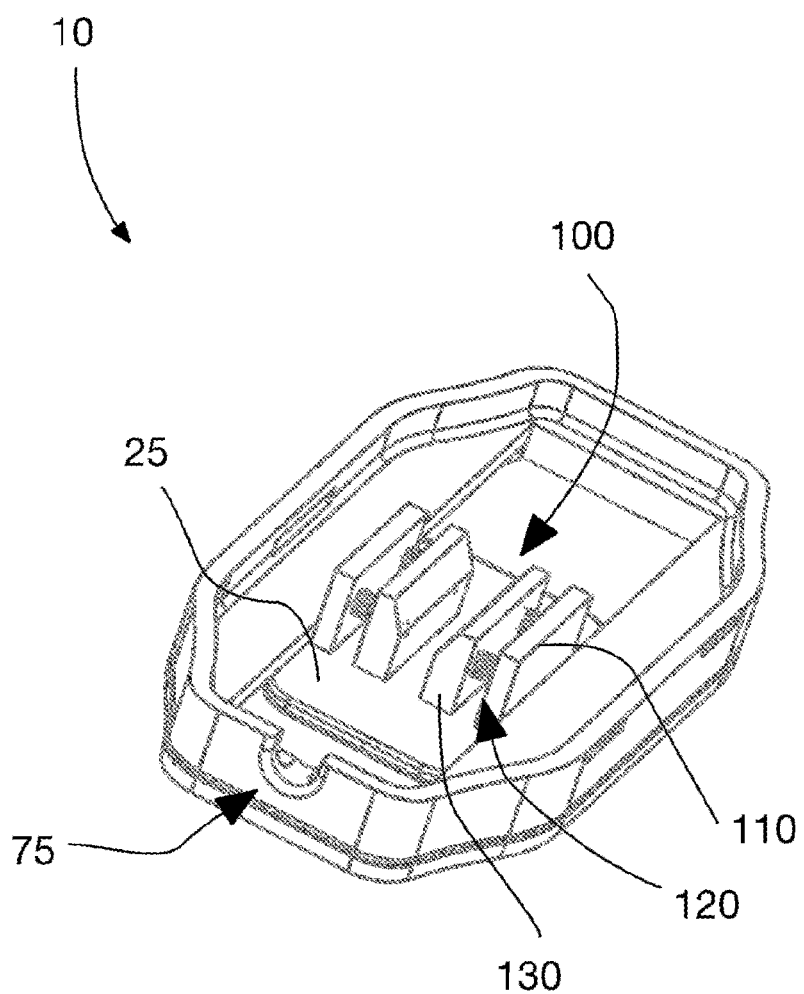
FIG. 6: Embodiment accommodating various catheter sizes.

The embodiment of FIG. 6 accommodates variation in catheter size. In this embodiment, the base of the sled 25 is shown along with features 110, 120 and 130 that may be used to accommodate the various sized catheters. For clarity, the lid and the other features described above are not shown. Feature 110 may be a stationary block immovable coupled to the bottom of the sled. Feature 130 may be a dynamic block; one or multiple springs may couple feature 130 to feature 110 such that the position of the dynamic block is always biased towards the middle of the device 10. Features 110, 120 and 130 may be placed on both sides of the central space 100. In operation, the catheter hub may be placed in the central space 100. Feature 130 may press against the catheter hub due to the spring forces; this configuration would then accommodate the various sized catheters as the position of the feature 130 would adjust according to the catheter diameter.

Figure 7:
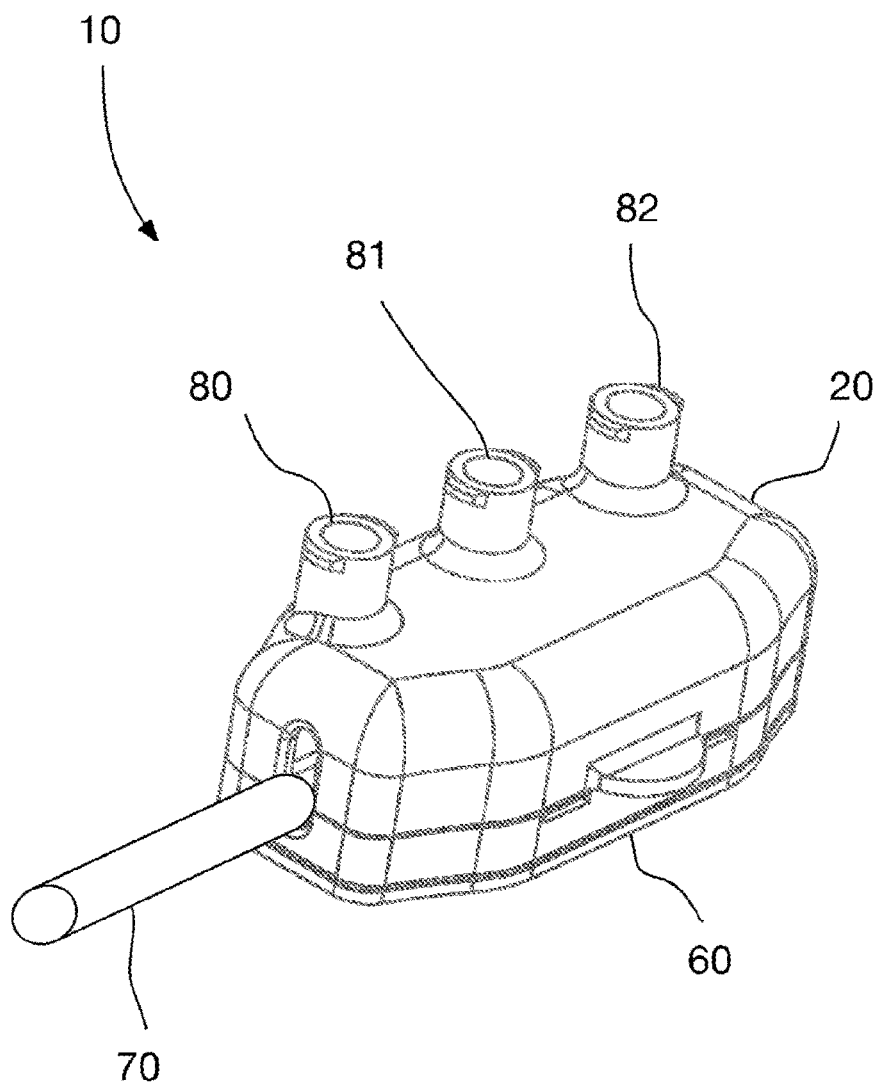
FIG. 7: Decoupling device with multiple inlets.

In a variation of the concepts above, the device 10 may have multiple inlets. FIG. 7 shows three inlets 80, 81 and 82. Internal to the device, each inlet may be coupled to the flexible/stretchable tubing (such as 30). Each tube may then be coupled to the catheter hub through its own luer connector. In this way, the decoupling device may decouple external motion even when multiple inlet ports are present. Although the figure shows three inlet ports, there may be more or fewer ports, such as 1, 2, 3, 4, 5, 6, 7 or 8.

In another variation, inline filters may be added in the path of the supply flow. These filters may be added in various locations such as in the catheter hub or in the flexible/stretchable tubing. These filters may filter out various unwanted components in the therapeutic supply such as but not limited to air bubble.

In yet another variation, sensors may be included within the device 10. These sensors may provide various functionalities, such as provide warnings. As an example, it may be possible that even with the decoupling device, the catheter still experiences a stress on both ends, for example, if the length of travel of the sled insufficiently large. A sensor may be placed on the sled that continuously senses if the sled reaches the end of its range. If so, the sensor may initiate a warning so that either the patient may become more cognizant of the situation and not flex his or her limb as much or the caregiver may choose a decoupler with a larger range of motion. Such a warning system would then minimize or eliminate the risk of the catheter dislodging from its site.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A catheter decoupling device comprising a catheter hub, sled and track, wherein:
   the hub comprises a proximal end configured to receive a catheter fluid supply device, and a distal end configured to receive a catheter;
   the sled receives and retains the hub;
   the track receives and retains the hub; and
   the hub has a limited range of back-and-forth motion relative to the track;
   further comprising a base and a lid, wherein the track is attached to, or is an integral part of the base, and the lid is configured to cover the hub, sled and track.

2. The decoupling device of claim 1 wherein the hub further has a limited range of side-to-side and/or up-and-down motion relative to the track.

3. The decoupling device of claim 1 wherein the limited range of back and forth motion is up to 50 mm.

4. The decoupling device of claim 1, wherein the lid is hinged and/or press-lockable to the base.

5. The decoupling device of claim 4 further comprising a flexible or stretchable tubing, wherein the proximal end of the hub is configured to receive the catheter fluid supply device via the tubing connected to the hub via a connector and connected to the catheter fluid supply device via an inlet port.

6. The decoupling device of claim 5, wherein the catheter fluid supply device is one of multiple fluid supply devices, and the inlet port is one of multiple inlet ports.

7. The decoupling device of claim 5 wherein the hub further has a limited range of side-to-side and/or up-and-down motion relative to the track, and the limited range of motion is up to 50 mm.

8. The decoupling device of claim 6 wherein the hub further has a limited range of side-to-side and/or up-and-down motion relative to the track, and the limited range of motion is up to 50 mm.

9. The decoupling device of claim 1 wherein the proximal end of the hub is configured to receive the catheter fluid supply device via a flexible or stretchable tubing connected to the hub via a connector and connected to the catheter fluid supply device via an inlet port.

10. The decoupling device of claim 9, wherein the device further comprises a bar around which the flexible or stretchable tubing is coiled.

11. The decoupling device of claim 9, wherein the catheter fluid supply device is one of multiple fluid supply devices, and the inlet port is one of multiple inlet ports.

12. The decoupling device of claim 9, wherein the catheter fluid supply device is one of multiple fluid supply devices, and the inlet port is one of multiple inlet ports connected to corresponding multiple lumens of the catheter, each lumen terminating in a distinctly located exit port.

13. The decoupling device of claim 9, wherein the catheter fluid supply device is one of multiple fluid supply devices, and the inlet port is one of multiple inlet ports connected to corresponding multiple lumens of the catheter, wherein the catheter comprise at least inner and outer multimaterial sheaths, wherein the inner surface of the inner sheath comprises a lubricious material.

14. The decoupling device of claim 9, wherein the catheter fluid supply device is one of multiple fluid supply devices, and the inlet port is one of multiple inlet ports connected to corresponding multiple lumens of the catheter, wherein the catheter comprises at least inner and outer multimaterial sheaths, wherein the inner sheath comprises an embedded coil.

15. The decoupling device of claim 1 further comprising a tensioned or tensionable movable block configured to retain within the device catheters of varying sizes.

16. The decoupling device of claim 1 wherein the hub further has a limited range of side-to-side and/or up-and-down motion relative to the track, and the limited range of motion is up to 50 mm.

17. A method of using the decoupling device of claim 1 comprising:
   connecting the proximal end of the hub to the catheter fluid supply device and the distal end of the hub to the catheter, wherein the device decouples the catheter from movement on the proximal side of the device.

18. A method of making the decoupling device of claim 1 comprising:
   assembling and connecting the hub, sled and track to form the decoupling device.

\* \* \* \* \*